(12) United States Patent
Nixon

(10) Patent No.: US 7,808,391 B2
(45) Date of Patent: *Oct. 5, 2010

(54) REMOTE CAREGIVER SUPPORT SYSTEM

(76) Inventor: Kenneth R. Nixon, 12323 Ash St., Overland Park, KS (US) 66209

( * ) Notice: Subject to any disclaimer, the term of this patent is extended or adjusted under 35 U.S.C. 154(b) by 79 days.

This patent is subject to a terminal disclaimer.

(21) Appl. No.: 12/156,755

(22) Filed: Jun. 4, 2008

(65) Prior Publication Data

US 2008/0316036 A1 Dec. 25, 2008

Related U.S. Application Data

(63) Continuation of application No. 11/245,800, filed on Oct. 6, 2005, now Pat. No. 7,411,510.

(60) Provisional application No. 60/618,334, filed on Oct. 14, 2004.

(51) Int. Cl.
*G08B 23/00* (2006.01)
*A61B 5/00* (2006.01)

(52) U.S. Cl. .............................. 340/573.1; 340/539.12; 340/825.19; 600/301; 128/920

(58) Field of Classification Search .............. 340/573.1, 340/539.12, 825.19; 600/300, 301; 128/904, 128/920; 348/155

See application file for complete search history.

(56) References Cited

U.S. PATENT DOCUMENTS

| | | | |
|---|---|---|---|
| 5,553,609 A | 9/1996 | Chen et al. | |
| 5,961,446 A | 10/1999 | Beller et al. | |
| 6,050,940 A | 4/2000 | Braun et al. | |
| 6,375,614 B1 | 4/2002 | Braun et al. | |
| 6,699,187 B2 | 3/2004 | Webb et al. | |
| 6,723,046 B2 | 4/2004 | Lichtenstein et al. | |
| 6,735,479 B2 | 5/2004 | Fabian et al. | |
| 6,753,782 B2 | 6/2004 | Power | |
| 6,875,174 B2 | 4/2005 | Braun et al. | |
| 6,947,411 B2* | 9/2005 | Parker et al. | 370/352 |
| 7,185,282 B1 | 2/2007 | Naidoo et al. | |
| 7,411,510 B1* | 8/2008 | Nixon | 340/573.1 |
| 2003/0069752 A1 | 4/2003 | LeDain et al. | |
| 2006/0033625 A1* | 2/2006 | Johnson et al. | 340/573.1 |
| 2008/0294462 A1* | 11/2008 | Nuhaan et al. | 705/3 |

OTHER PUBLICATIONS

Internet Web page article entitled "QuiteCare[SM] puts its powerful technology to work protecting seniors at home," www.quitecaresystems.com, Living Independently Group, Inc., 4 pp. (2004).

* cited by examiner

*Primary Examiner*—Toan N Pham
(74) *Attorney, Agent, or Firm*—Dunlap Codding, P.C.

(57) ABSTRACT

The current invention provides a remote caregiver support system which allows caregivers to provide informal care to care receivers. The systems of the current invention comprise a caregiver system and a care receiver system operating on personal computers. Each system is linked by a communications network. Preferably, the communications network is a high speed internet connection. Additionally, the current invention provides methods for delivering informal care to a care receiver remotely located from the caregiver. In the methods of the current invention, the caregiver accesses a remote caregiver support system and interacts with the care receiver providing text reminders and other informal care necessary to ensure the continued health and wellbeing of the care receiver.

55 Claims, 7 Drawing Sheets

REMOTE CAREGIVER SUPPORT SYSTEM

CROSS-REFERENCE TO RELATED APPLICATION

This application is a continuation of U.S. Ser. No. 11/245,800, filed Oct. 6, 2005, now U.S. Pat. No. 7,411,510 which claims priority from U.S. Provisional Patent Application Ser. No. 60/618,334 filed on Oct. 14, 2004, the entire contents of both patent applications are hereby expressly incorporated by reference in their entirety.

STATEMENT REGARDING FEDERALLY SPONSORED RESEARCH OR DEVELOPMENT

Not Applicable.

FIELD OF THE INVENTION

The current invention is a remote caregiver support system designed to enable the provision of remote assistance or informal care, such as that provided by a family caregiver. The current invention can be used to meet the needs of older adults or individuals suffering from chronic or disabling conditions, such as Alzheimer's disease, and allow care receivers to live independently in comfortable and familiar surroundings as long as possible. Further, the current invention addresses the needs of the caregiver, such as the need to balance work, family and caregiving responsibilities and minimizes disruption to the caregiver's daily routine while enhancing the quality and quantity of care provided on a daily basis to the care receiver.

BACKGROUND OF THE INVENTION

Older adults, including individuals in early stages of Alzheimer's and other chronic conditions, are frequently capable of living independent lives provided that an adequate support system exists to meet their informal care needs. Family members typically assume the responsibility for providing such support and supervision. Unfortunately, given the time consuming nature of caregiving, some caregivers may not be able to provide the care required, especially long-distance caregivers. As a result, some care receivers may move prematurely into assisted living or other costly supported living arrangements. Caregivers frequently travel an hour or more to provide the support required by their loved ones. Currently, about 7,000,000 Americans are classified as long-distance caregivers for their older relatives with an average travel time of four hours.

As used herein, the term "informal care" refers to the provision of active support, social interaction and protective supervision by a caregiver to a care receiver. For example, the term caregiver refers to an individual such as a family member, relative, friend or a professional in-home care provider who provides assistance to an older adult or individual suffering from a chronic condition, i.e., the care receiver. As the caregiver role evolves and turns into a major time-consuming responsibility, the continual stress can create personal, health and financial hardships.

In 2004, studies estimated there are 44.4 million American caregivers. While these services are generally unpaid, their value has been estimated to be approximately $257,000,000,000 annually. Clearly, informal care provided by family caregivers is the underpinning of long-term care in the United States. As such, there is a need for a system that provides a cost effective caregiver intervention alternative that meets the needs of the caregivers, especially long-distance caregivers, and permits a caregiver to provide the necessary informal care to a care receiver.

SUMMARY OF THE INVENTION

In one embodiment, the current invention relates to a system for providing remote informal care to at least one individual care receiver. The system comprises a caregiver system and a care receiver system configurable by the caregiver system. The system further comprises a communication network linking the caregiver system and the care receiver system, wherein the care receiver system is operable in an unattended mode whereby the care receiver provides no input to and interacts with the care receiver system.

In another embodiment, the current invention relates to a care system comprising a caregiver system having a first personal computer system and a caregiver client. The care system further comprises a care receiver system having a second personal computer system and a care receiver client. The care receiver client and the caregiver client enable interaction between the caregiver system and the care receiver system via a communication network. The caregiver client enables a caregiver to remotely establish a videoconference between the care receiver system and the caregiver system and at least one of the following: a reminder on the care receiver system, a slideshow on the care receiver system, and a journal entry on the care receiver system.

In another embodiment, the current invention relates to a method of providing remote informal care to a care receiver. The method comprises establishing communication via a network between a caregiver system having a caregiver client and a care receiver system having a care receiver client. The method further comprises configuring the care receiver client with the caregiver client. The method further comprises providing at least one of the groups of: establishing a reminder on the care receiver system; establishing a videoconference between the care receiver system and the caregiver system; displaying a slideshow on the care receiver system; and establishing a journal entry on the care receiver system.

In another embodiment, the current invention includes a method of providing informal care to at least one care receiver at a separate location from a caregiver. The method comprises communicating via a network between a caregiver system and a care receiver system, the care receiver system comprising a care receiver client. The method also comprises establishing a videoconference between the caregiver system and the care receiver system in an interactive mode or in an observational mode. The method further comprises resetting the videoconference on the care receiver system with a caregiver client associated with the caregiver system.

DETAILED DESCRIPTION OF THE PREFERRED EMBODIMENTS OF THE INVENTION

Figure 1:
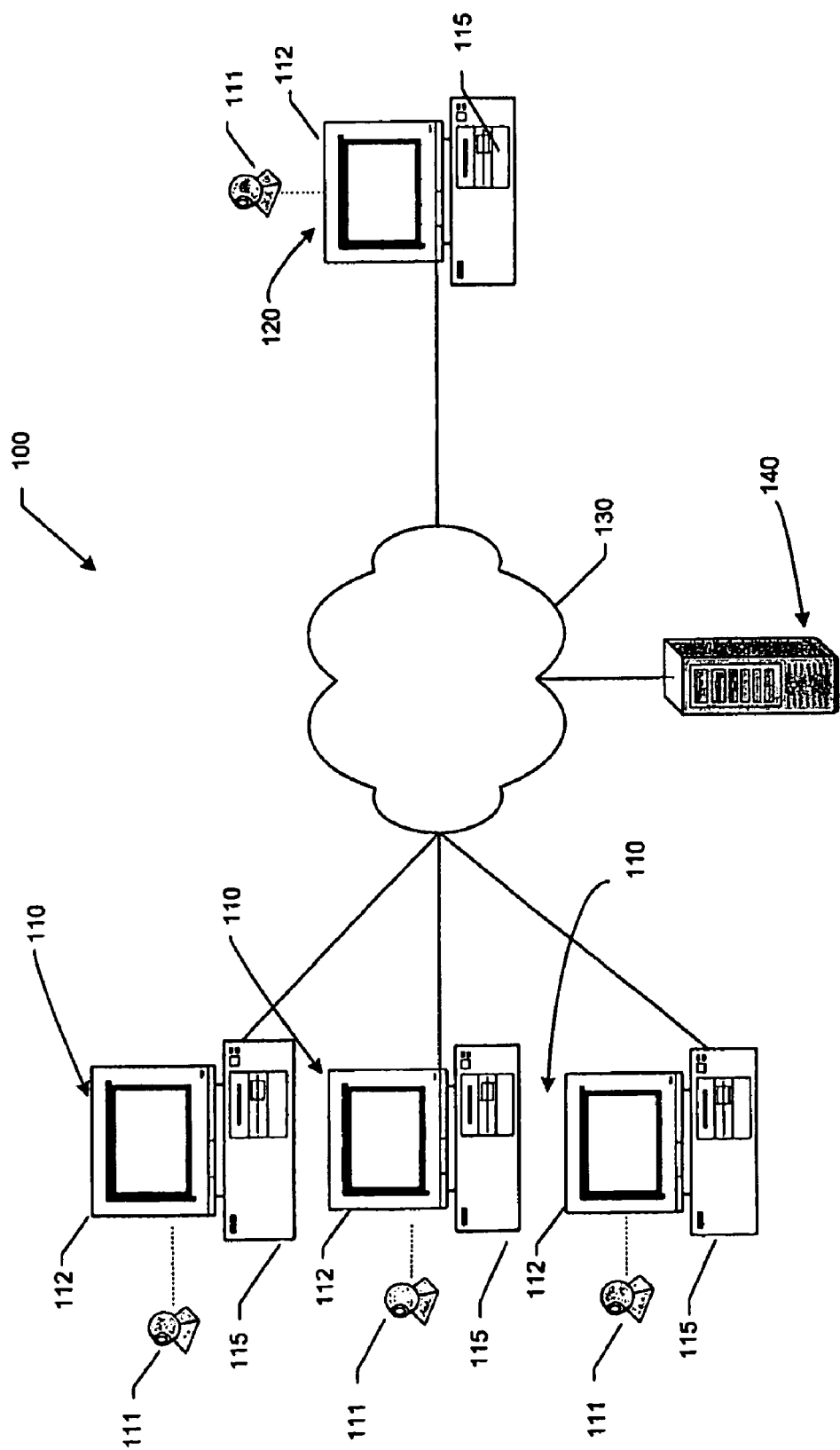
FIG. 1 is a schematic diagram showing a preferred embodiment of the current invention.

With reference to the drawings, the current invention provides a remote caregiver support system 100. Remote caregiver support system 100 can be configured for multiple caregivers and multiple care receivers. Thus, FIG. 1 depicts one preferred embodiment of the current invention wherein multiple caregivers interact with and support a single care receiver. Although not depicted, the current invention contemplates other configurations where multiple caregivers interact with and support multiple care receivers or where a single caregiver supports multiple care receivers.

With reference to FIG. 1, the remote caregiver support system 100 comprises three primary components, a caregiver system 110, a care receiver system 120 and a communications network 130. Preferably a central server 140 is linked to the caregiver system 110 and the care receiver system 120 by communications network 130. For the purposes of this disclosure, the preferred communications network 130 is the Internet. However, any communication system such as a satellite system, closed circuit cable system, wireless network or other communications system will be suitable for supporting the systems and methods disclosed herein.

The hardware and software comprising both the caregiver and care receiver systems 110, 120 are under the general control of a standard software operating system. In a preferred embodiment of the invention, the operating system is the Windows® operating system, sold and distributed by the Microsoft Corporation. However, other operating systems may be used without departing from the scope of the invention. Further, coding necessary for controlling and manipulating each of the software systems and hardware components utilized in the current invention will be within the abilities of one skilled in the art.

Figure 3:
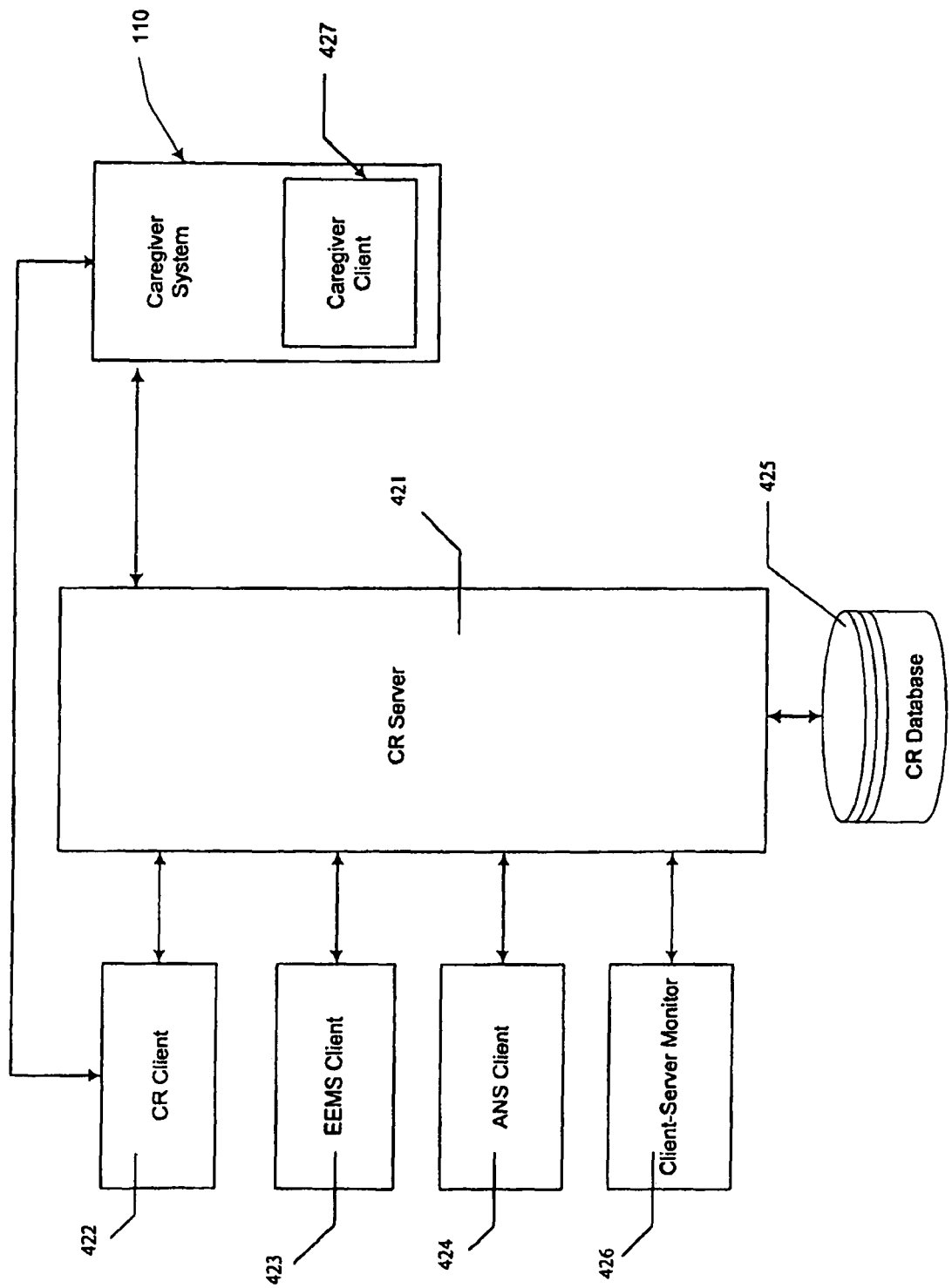
FIG. 3 is a schematic diagram showing the interaction between the care receiver system and the caregiver.
Figure 4:
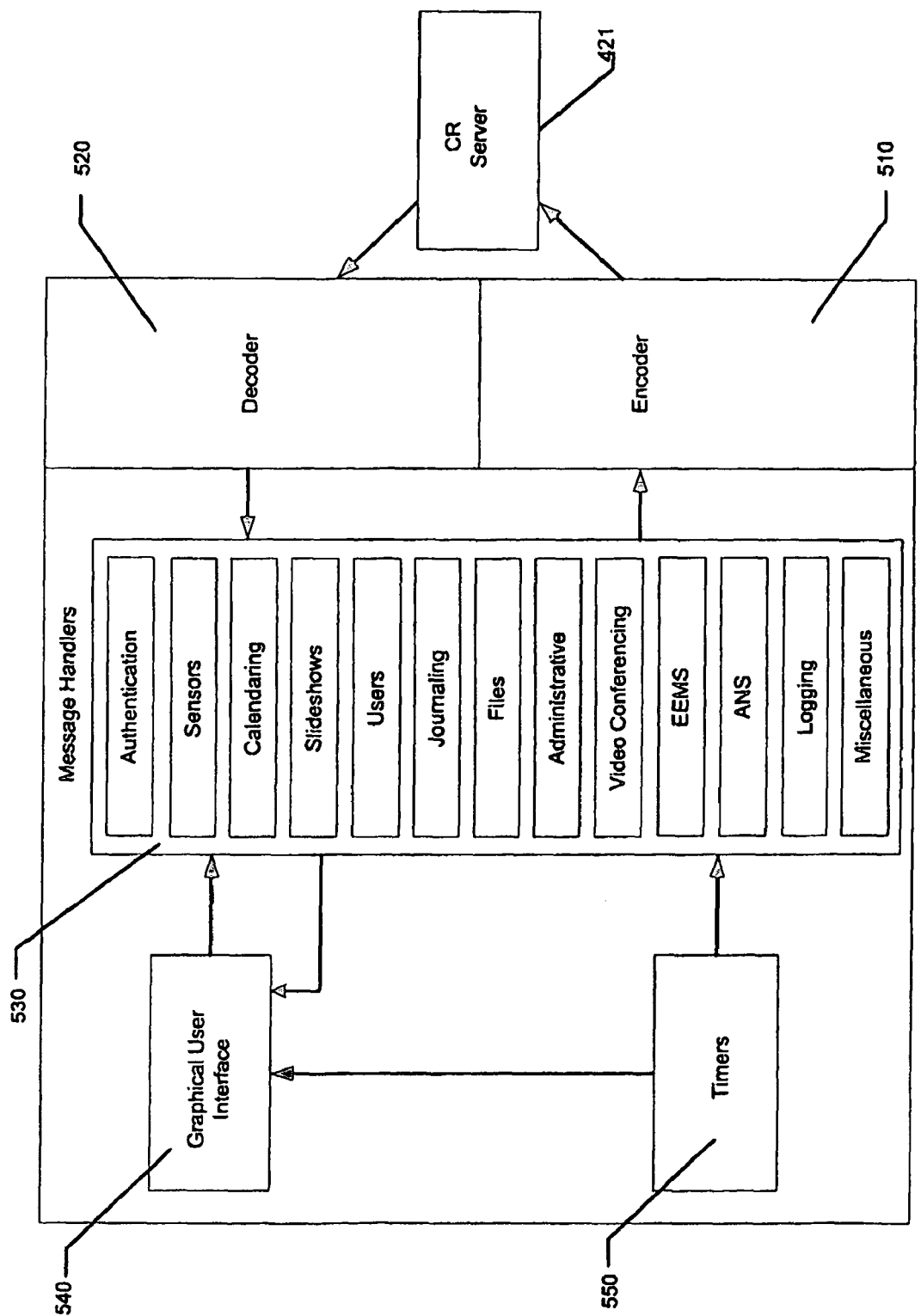
FIG. 4 is a schematic diagram showing the functional details of the care receiver client and the CG client.
Figure 5:
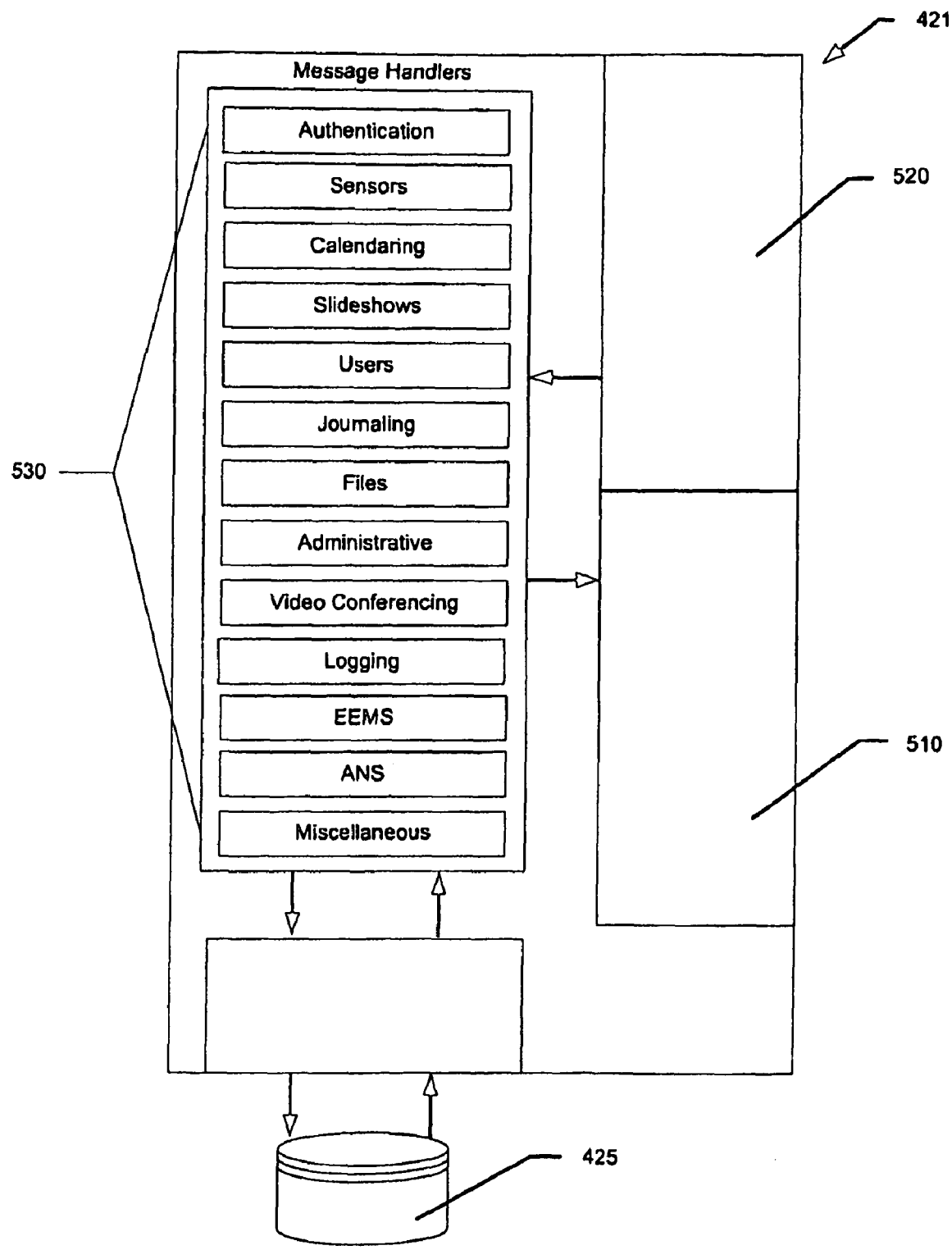
FIG. 5 is a schematic diagram showing the functional details of the care receiver.

The primary components of caregiver system 110 are depicted in FIGS. 1, 3 and 4. In a preferred embodiment, caregiver system 110 comprises a personal computer 115, a video camera 111, a monitor 112 and a microphone (not shown). While the remainder of this disclosure will focus on a caregiver system 110 utilizing personal computer 115, the use of other devices such as handheld devices, including but not limited to Palm® devices, Blackberry® devices and mobile phones having suitable capabilities, are also contemplated by this invention. Web-TV®, provided by Microsoft Corp., may also be adapted to serve in place of personal computer 115.

Personal computer 115 provides the means for running the supporting software necessary for carrying out the caregiving tasks and fulfilling the needs of the caregiver and care receiver. In particular, a software package referred to herein as the caregiver client 427 is loaded onto personal computer 115. The caregiver client 427 provides the functionality necessary to permit the caregiver to remotely support and supervise the care receiver. In the preferred embodiment, the caregiver client 427 includes a videoconference capability suitable for supporting interactive videoconferences between the caregiver and the care receiver. Additionally, the videoconferencing capability preferably permits the caregiver to view the care receiver or care receiver's living environment in an observational mode. Thus, as used herein "videoconference" includes audio and video transmitted from one or more care receiver systems to one or more caregiver systems such as in observational mode, but it may also include audio and video transmitted from one or more caregiver systems to one or more care receiver systems such as in interactive mode. "Videoconference" as used herein also includes videoconferences between caregivers. The functionality provided by the caregiver client 427 will be discussed in further detail below with regard to the methods of the current invention.

The primary components of care receiver system 120 are depicted in FIGS. 1, 2, 3 and 4. In a preferred embodiment, care receiver system 120 comprises a personal computer 115, a video camera 111, a monitor 112 and a microphone (not shown). As in the caregiver system 110, personal computer 115 may be replaced by any suitable communication device capable of providing interactive communication between the care receiver and the caregiver including but not limited to Palm® devices, Blackberry® devices and mobile phones having suitable capabilities. As a non-limiting example, Web-TV®, provided by Microsoft Corp., may be adapted to serve in place of personal computer 115.

Figure 2:
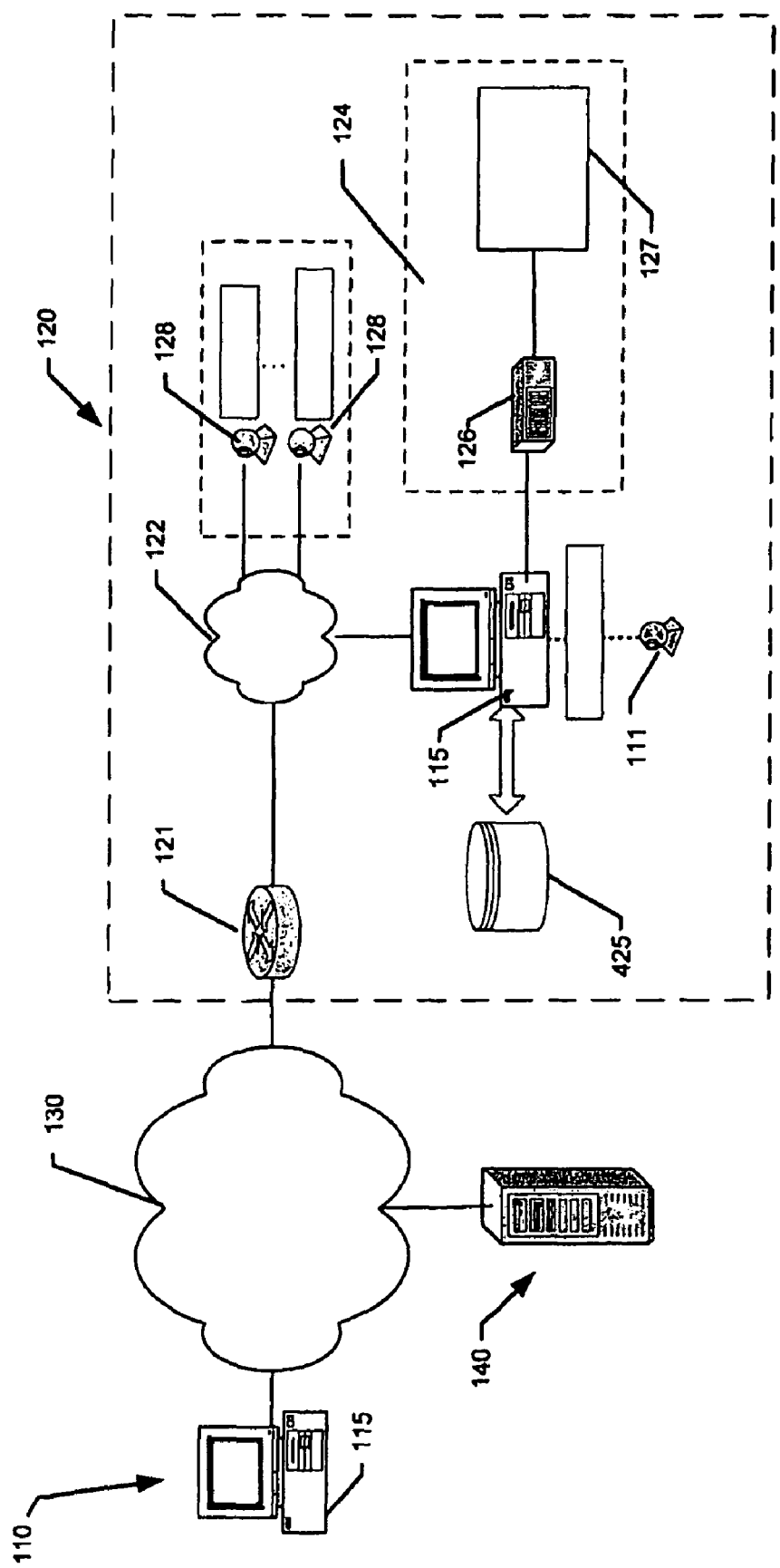
FIG. 2 is a schematic diagram in which the care receiver component includes environmental sensors.
Figure 7:
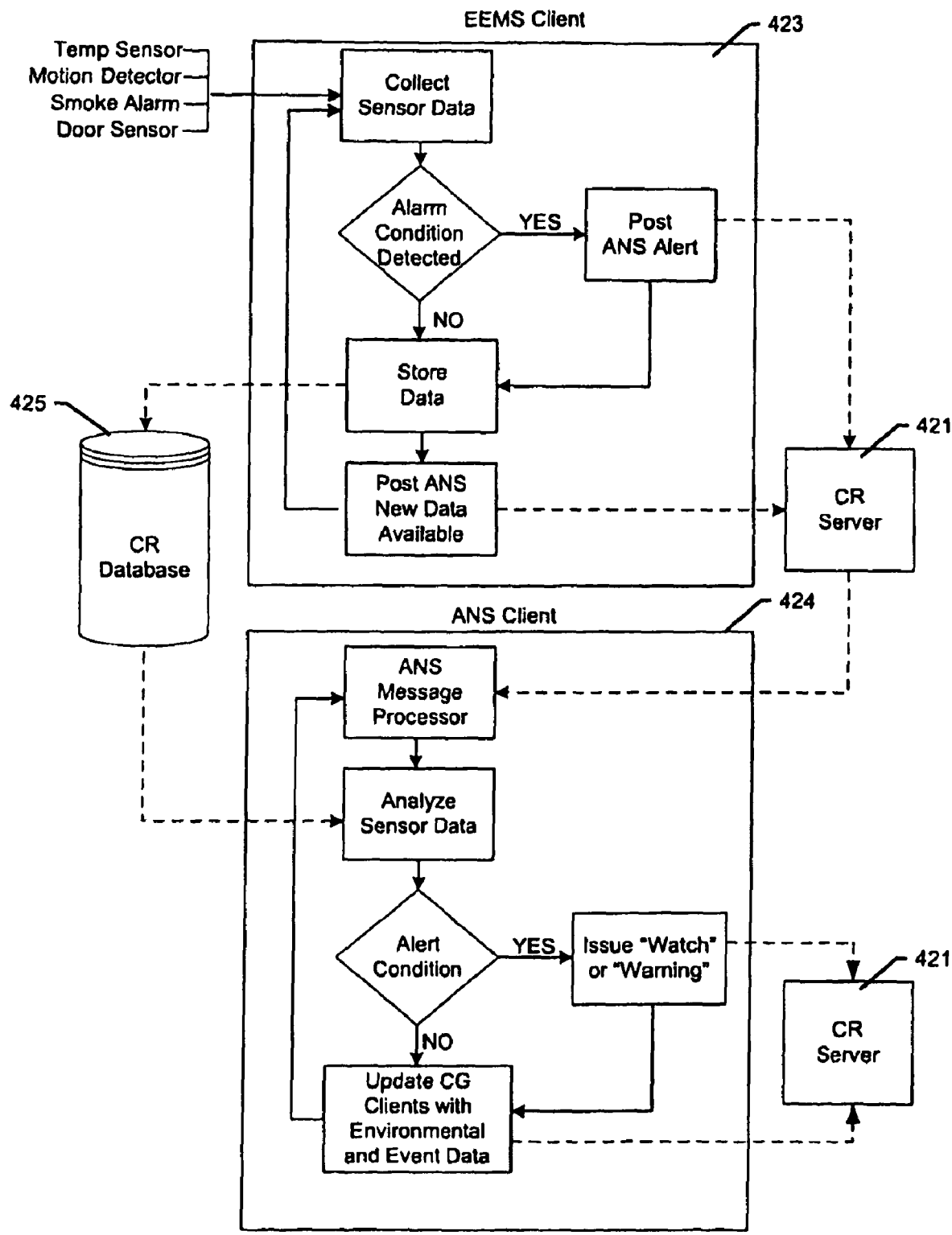
FIG. 7 is a flowchart of a method of operation of the environmental and event monitoring subsystem and the alert notification system, according to an embodiment of the invention.

Care receiver system 120 utilizes a software package known as the care receiver client 422. Care receiver client 422 is preferably configured to run in either attended mode or unattended mode. When operating in the unattended mode, care receiver client 422 enables operation of care receiver system 120 without any input or computer skills on the part of the care receiver. Optionally, as depicted in FIG. 2, care receiver system 120 may include an environmental and event monitoring system (EEMS) 124 and software packages known as an environmental and event monitoring system client (EEMS client) 423 and an alert notification system client (ANS client) 424. EEMS 124 preferably comprises an EEMS server 126 and at least one sensor 127 suitable for monitoring the environment at the care receiver's residence. More preferably, EEMS 124 comprises multiple sensors 127. Sensors 127 provide the ability to monitor temperature, motion, detect smoke and determine the status of doors/windows in the care receiver residence. In a preferred embodiment, the EEMS client 423 receives data from sensors 127 and stores the data in the care receiver database 425. The data is subsequently analyzed by the ANS client 424. Additionally, the ANS client 424 provides the means for sending alerts for predefined situations to the caregivers. Notification of caregivers may be made in a priority sequence and in the media selected by each caregiver. For example, caregivers may receive emails, including email sent to mobile phones, or telephone messages. FIG. 7 provides a computer flow diagram depicting a preferred embodiment of the relationship between the EEMS client 423 and the ANS client 424.

In a preferred embodiment care receiver system 120 preferably includes a care receiver database 425. Care receiver database 425 stores system and application data including all profile settings, reminders, slideshows, user information and other information necessary to the operation of the current invention. For example, relevant information developed by sensors 127 and other data generated by care receiver system 120 will be stored in care receiver database 425 for access by the caregiver.

Optionally, care receiver system 120 includes a local intranet 122 comprising at least one auxiliary video camera 128 and a router 121. In the preferred embodiment, local intranet 122 is directly accessible via router 121 by caregiver system 110.

Referring now to FIG. 3, in the preferred embodiment, care receiver system 120 includes a separate software program acting as a "software server" referred to herein as the care receiver server 421. Care receiver server 421 provides message handling, updates to data in the database 425 and handles requests for data from the database 425. In particular, care receiver server 421 provides an interface for communications between care receiver client 422 and components such as EEMS 124, the ANS client 424, and caregiver system 110. Each of these clients sends messages to the care receiver server 421 along with the appropriate credentials. Care receiver server 421 then checks the credentials prior to processing the message in order to maintain system security. FIG. 3 provides a flow diagram depicting the communication routes associated with care receiver server 421.

Additionally, client server monitor software program monitors care receiver client 422 and care receiver server 421 for operation within acceptable parameters. If the client server monitor detects that care receiver client 422 or care receiver server 421 is unresponsive or operating outside of the acceptable, predetermined parameters, then the client server monitor will shut down and restart care receiver client 422.

FIG. 4 depicts in block diagram various elements common to the care receiver client 422 and caregiver client 427. These elements include message encoder 510 and message decoder 520 suitable for providing communication between caregiver client 427 and care receiver server 421 and between care receiver client 422 and care receiver server 421. In the preferred embodiment, message decoder 520 receives messages from care receiver server 421, decodes the message and communicates it to the appropriate message handler 530. Message handler 530 assigns the message to the appropriate category and implements the desired procedure. For example, as depicted in FIG. 4, a non-limiting list of categories would include: authentication, sensors, calendaring, slideshows, users, journaling, files, administrative, videoconferencing, EEMS, ANS, logging and miscellaneous. Message handlers 530 are also in communication with the graphical user interface 540 and the timers 550 provided by each caregiver client 427 and care receiver client 422. Graphical user interface 540 implements the desired command for the respective caregiver or care receiver system 110, 120. In general, timers 550 provide reminders in the form of programmed interrupts of preset events for either or both the care receiver and caregiver. Typically, reminders created by the caregiver are activated by timers 550 and are displayed as text with flashing background or other demonstrative event on the care receiver's graphical user interface 540.

In the preferred embodiment of remote caregiver support system 100, communications network 130 links caregiver system 110 with care receiver system 120. Additionally, the preferred embodiment of the current invention includes a central server 140. Central server 140 provides data that enables the connection of caregiver and care receiver systems 110, 120. Preferably central server 140 includes software suitable for providing data collection, data storage and other typical server functions.

Finally, remote caregiver support system 100 may optionally include a technical support computer (not shown). Preferably, technical support computer provides the capability to remotely diagnose and troubleshoot problems in support of the caregiver. In the preferred embodiment, the technical support computer is linked to central server 140 via communications network 130.

The methods of the current invention will be described with continued reference to the drawings. In the methods of the current invention, remote caregiver support system 100 provides the caregiver(s) with the ability to interact with the care receiver(s) remotely. As noted above, remote caregiver support system 100 can be configured to support single or multiple caregivers supporting one or more care receivers.

For the sake of clarity, the remainder of this disclosure will describe the methods of the current invention with reference to a configuration wherein multiple caregivers provide informal care to a single care receiver as depicted in FIG. 1.

The following description of the methods of the current invention assumes that the care receiver client 422 and caregiver client 427 software have been properly installed on each personal computer 115. Following installation of the relevant software on each personal computer 115, caregivers must be designated as authorized users on care receiver system 120. Caregivers are assigned an account on care receiver system 120. Preferably, the primary caregiver account is established when care receiver client 422 is first installed on the care receiver system 120. Additional users can be added at any time by a primary caregiver. The account includes a password and user identification for each caregiver. The list of authorized users and passwords are stored in the care receiver database 425 of care receiver system 120. Additionally, the network address for care receiver system 120 is retrieved by accessing central server 140 and providing a software license number or equivalent access number corresponding to care receiver system 120.

Following establishment of the network address for care receiver system 120, the caregiver must logon to caregiver system 110 using the caregiver client 427. During the logon process, the caregiver's user name and password are transmitted to care receiver server 421. Provided that the user name and password are accepted by care receiver server 421, a communication channel is established between caregiver system 110 and care receiver system 120 over communications network 130. Preferably, the communication channel is a secure channel suitable for protecting the privacy of the parties. Optionally, a caregiver may log on to the care receiver system 120 in "invisible mode" thereby permitting use of the system without alerting other users or the care receiver that the caregiver is logged-in.

Following establishment of the secure communication channel, the primary caregiver will have access to care receiver system 120 on the care receiver's personal computer 115. The primary caregiver configures care receiver system 120 to suit the needs of the caregivers and the care receiver. As an initial step, the caregiver preferably creates accounts for other users. When establishing these accounts, the primary caregiver will identify the type of user, either a primary caregiver or caregiver, and set the rights and privileges for each caregiver authorized to access care receiver system 120.

Subsequently, the caregiver uses the caregiver client 427 to customize both caregiver system 110 and care receiver system 120 to the particular needs of the caregivers and care receiver. When working in a Windows® environment, the caregiver client 427 will preferably have a clickable button labeled "settings" which initiates the functionality for customizing the global configurable parameters, creating the desired environment on caregiver system 110 and care receiver system 120. Accessing the settings button on the caregiver client 427 allows the caregiver to modify the global configurable options of the care receiver system 120. In particular, the caregiver can change the care receiver's display settings for the clock, the location of the video display on monitor 112 and font sizes as they appear on the care receiver's monitor 112. Thus, the settings button allows the caregiver to alter the care receiver's graphical user interface 540 displayed on the care receiver's monitor 112.

Further, the settings button permits changes to be made in the care receiver's operation and privacy settings. For example, care receiver system 120 may operate in either attended or unattended modes. Additionally, video sessions may operate in observation mode or interactive mode. Settings to allow or not allow observation mode video sessions are controllable from the settings button accessed through the caregiver client 427. Care receiver system 120 can be set to automatically accept videoconference sessions and the time of day specified when such sessions will be permitted.

The settings button also permits configuration of the care receiver's graphical user interface settings in order to permit easier reading of reminders and other text displayed on monitor 112. The settings button also enables changes to the care receiver's multimedia settings such as the sound volume on the care receiver system when not in a videoconferencing and slide transition timing. Additionally, changes to the videoconference setup are also enabled through the settings button. For example, the settings button permits selection of the video capture device used and fine tuning videoconferencing quality parameters. Moreover, the caregiver can change the care receiver's display settings for the clock, the location of the video display on monitor 112 and font sizes as they appear on the care receiver's monitor 112.

The settings button also enables changes in the care receiver's reminder settings. For example, the caregiver may elect to play a sound for certain critical reminders. Additionally, if a new reminder has been added, the caregiver may elect to play a sound and incorporate background flashing or other visual techniques to alert the care receiver to a new reminder being displayed. Preferably, audible sounds, including a distinctive chime or a recording of the caregiver's voice, will be available to alert the care receiver of important information being displayed or task to be performed. Finally, the volume and repetition rate of the alerting audio is managed by the caregiver through the settings button.

The caregiver client 427 also provides the ability to control overall operations of care receiver system 120. If the caregiver detects a problem when interacting with care receiver system 120, then the caregiver has several options available for correcting the problem. If remote caregiver support system 100 includes a technical support computer, then the caregiver may contact the technical support computer via communications network 130 and describe the problem discovered on caregiver system 110 or care receiver system 120 seeking a response and instructions for correcting the problem. Alternatively, the caregiver may use the troubleshooting window provided by the caregiver client 427. Through the troubleshooting window, the caregiver may elect to reset the videoconferencing system, restart care receiver client 422 or reboot the care receiver system 120. Any of these tasks are easily carried out by selecting the proper command and then clicking the appropriate button as is common to Windows® programs.

Preferably the caregiver will receiver notification of software updates and may download and the updates that will be applied automatically to both the caregiver system 110 and the care receiver system 120.

Following establishment of the desired settings on care receiver system 120, the primary caregiver will preferably use the caregiver client 427 to add new users to care receiver server 421. In a preferred embodiment the caregiver will enter a username and a display name for each new user. Further, the primary caregiver will identify each new user as either a primary caregiver or a caregiver. Additionally, the primary caregiver will choose a password for each new user which will also be stored in the care receiver database 425.

For the purposes of this disclosure, a primary caregiver can perform all the administrative tasks described above with regard to the settings on care receiver system 120, including restricting the use of other caregivers to the system. As such, the primary caregiver establishes the times and days of the week when the other caregiver users may access care receiver system 120. Additionally, the primary caregiver has the ability to remove a user from care receiver system 120. In the preferred embodiment, a separate window is used to establish the allowable log-in times for each caregiver user. A separate window enables easy alteration of login restrictions for each caregiver user. Finally, the primary caregiver has the ability to view usage reports reporting videoconferencing activity per day per caregiver.

Once new users have been added to care receiver system 120 and stored in the care receiver database 425, each authorized user, within restrictions set by the primary caregiver, will have the ability to access care receiver system 120 and add content to care receiver system 120. When viewing the caregiver client 427 graphical user interface, a caregiver will be able to identify other authorized users and will be able to determine their online or offline status. Further, the caregiver client 427 will depict whether or not any caregivers are currently in a videoconference. In the preferred embodiment of the current invention caregivers may videoconference with any care receiver and with any caregiver.

The ability to videoconference with the care receiver enhances the interactive nature of remote caregiver support system 100. Once a caregiver has started the caregiver client 427 program and has logged-on to the care receiver client 422, the caregiver may initiate a videoconference with other users online. In one preferred embodiment the caregiver may select a user with which to videoconference and click on a "call" button to initiate the videoconference. Thus, the present invention allows for videoconferencing between the various caregivers without inclusion of the care receiver. This feature allows remote caregivers to meet online in order to discuss and enhance the provision of care to the care receiver.

If the videoconference is to be with the care receiver, then the caregiver preferably has the option of starting the videoconference in observation mode or interactive mode. When starting a videoconference in observation mode, the care receiver's video and audio are transmitted to the caregiver without displaying the caregiver's video or audio to the care receiver. Thus, activation of the observation mode permits the caregiver to hear and see activity within the care receiver's residence without interrupting the care receiver's daily activities. Preferably the caregiver client 427 interacts with care receiver client 422 to permit dynamic switching from observation mode to interactive mode once the videoconference connection has been established between the caregiver client 427 and the care receiver client 422.

Once the interactive videoconference mode has been entered by the parties, each party can observe the other party on their monitors 112. However, the care receiver system 120 will not require input or computer skills by the care receiver. Each system is provided with speakers and microphones (not shown) which permit communication between the parties. Through the videoconferencing interface on the caregiver client 427, the caregiver can dynamically control multimedia settings on care receiver system 120 such as the care receiver's microphone sensitivity and speaker volume as well as microphone sensitivity and speaker volume associated with the caregiver system. These adjustments may be made dynamically during the videoconference. Additionally, as noted above during the discussion of settings, the caregiver client 427 enables the caregiver to control the size of the video window and the time of day to accept videoconferencing. Preferably, on conclusion of a videoconference, the caregiver client 427 stores the multimedia settings and restores these settings upon initiation of the next videoconference. In a preferred embodiment the caregiver client 427 enables previewing of the image to be seen by the care receiver. Thus the caregiver client 427 ensures that the image transmitted to the care receiver is the image desired by the caregiver. In this manner, the caregiver can adjust camera 111 forming part of caregiver system 110 for correct positioning and focus for the image being transmitted and projected to the care receiver. Additionally, in a preferred embodiment, the caregiver will be able to dynamically control during the videoconference the pan and tilt of the camera 111 incorporated into care receiver system 120. Preferably, at least four preset pan and tilt settings set by the caregiver will be available for selection by the caregiver. Control of the pan and tilt of camera 111 is provided by the interaction of the caregiver client 427 with the care receiver server 421.

Preferably the videoconference takes place over a separate videoconferencing channel established between the caregiver client 427 and care receiver client 422. This separate channel has a secure channel also on, or supported by, communication network 130 but taking the form of a virtual private network ("VPN"). As with the other settings, the VPN may be managed by the caregiver client 427 which provides the ability to reset the VPN using the troubleshooting window of the caregiver client 427.

In addition to providing the caregiver with the ability to interact directly with the care receiver via videoconferencing, the caregiver client 427 also provides the caregiver with the ability to provide support to the care receiver through the establishment of slideshows, reminders and visual cueing. The ability to create, edit and display slideshows for the benefit of the care receiver helps the care receiver remain connected to and engaged in family activities. The ability to establish reminders and display images for visual cueing for the care receiver helps the care receiver to function more independently. The reminders, in conjunction with the clock and calendar on the graphical user interface 540 on care receiver system 120, assist the care receiver in daily self care. Finally the care receiver client 422 provides an online journal, which allows the caregivers to create a log relating to observations about the health and wellbeing of the care receiver and to communicate important information among caregivers. Access to the journal may be shared between caregivers, and caregivers will be notified of new entries in the journal. Preferably, notices of new journal entries will be provided automatically upon access of the caregiver client 427.

Using the caregiver client 427, caregivers can create slideshows which help the care receiver remain connected with family and friends. In the preferred embodiment, the caregiver client 427 includes a button or tab labeled "slideshows" which permits the addition, removal or editing of a slideshow. The caregiver creates the slideshow using the caregiver client 427 and the caregiver system 110. Slides within the slideshow may be rearranged, removed or added as desired by the caregiver. Following creation of the slideshow, the caregiver preferably uploads the slideshow images to care receiver system 120 where they are stored in care receiver database 425.

Other caregivers having access to care receiver's system 120 will be notified of the addition of new slides to slideshows currently active on the care receiver's system. Slideshows may be activated at any time by the caregiver, including during a videoconference with the care receiver. Slides and images being displayed on the care receiver client 422 are simultaneously displayed on all caregiver clients 427 currently online. The slideshow feature within the caregiver client 427 provides for the capability to override the slideshow sequence and select a given slide or image to be displayed on the care receiver's system. Thus the slideshow feature further enhances interaction between the caregiver and the care receiver. In the preferred embodiment when a caregiver logs into remote caregiver support system 100 and accesses care receiver's system 120, new slides added to active slideshows will be subsequently downloaded to the caregiver's respective caregiver system 110.

The reminders feature provided by remote caregiver support system 100 is a critical feature which enhances the care receiver's capability to function more independently. Reminders may be one of three types: informational, to do, and special. An "informational" reminder is displayed on the screen but this type of reminder makes no effort to attract the care receiver's attention. In contrast, the "to do" reminder attempts to bring attention to itself by generating an audible sound and/or flashing to attract the care receiver's attention. Preferably, caregiver client 427 provides for the recording of the caregiver's voice to serve as the sound to be played when a "to do" reminder is displayed. In the preferred embodiment "informational" and "to do" reminders are displayed in a portion of care receiver's graphical user interface 540. "Special reminders" however, are displayed in a unique manner designed to quickly gain the attention of the care receiver. Preferably special reminders will be accompanied by a distinct audible sound different from the sound normally used for a "to do" reminder. Reminders may be set to be displayed at any time of day, any day of the week and on a recurring pattern.

As with the other functions in the caregiver client 427, a button or tab is preferably provided for initiating the reminders feature of the caregiver client 427. By clicking on the "reminders" button or tab, the caregiver will be provided with the means for establishing and editing the three types of reminders. If reminders are overlapping with one another, then the caregiver client 427 preferably provides for the display of multiple reminders by cycling from one to another as specified in the global settings set by the caregiver. In this manner the care receiver is not overwhelmed by multiple tasks to be performed at the same time. Thus, the present invention provides an easy and timely manner for caregivers to inform and remind the care receiver of tasks that need to be performed. In addition, text reminders may be coupled with images to provide visual cueing to show the care receiver the action to be preformed. The performance of these tasks by the care receiver provides a feeling of independence and a sense of accomplishment and self-worth.

As noted above, the caregiver client 427 also provides for the maintenance of a journal relating to the caregiver's interaction with the care receiver. Preferably the journal is searchable thereby allowing each caregiver to view entries by other caregivers. Additionally, the journal records all "to do" reminders that have been displayed and also indicates whether the reminder was or was not acknowledged by the care receiver. The journal also stores contacts and medications relating to the care receiver in the care receiver database 425. For example, the contacts data in the care receiver database 425 may be populated with friends and neighbors, service organizations, and healthcare professionals familiar with the care receiver's condition including but not limited to personal physicians, dentists and emergency care providers. Further, care receiver database 425 may also be used to store medication data for medications currently being taken by the care receiver and to create a complete record of previously taken medications. Preferably, journal entries in the care receiver database 425 are editable and searchable by the caregivers in accordance with the permissions given them by the primary caregiver. Journal entries may also be used to log observations and memorialize discussions with and regarding the care receiver, including observations and discussions which occurred during videoconferences between the caregiver and the care receiver. The journal entries preserve these observations and discussions, including the date they occurred, and makes these entries available for other caregivers to review.

Figure 6:
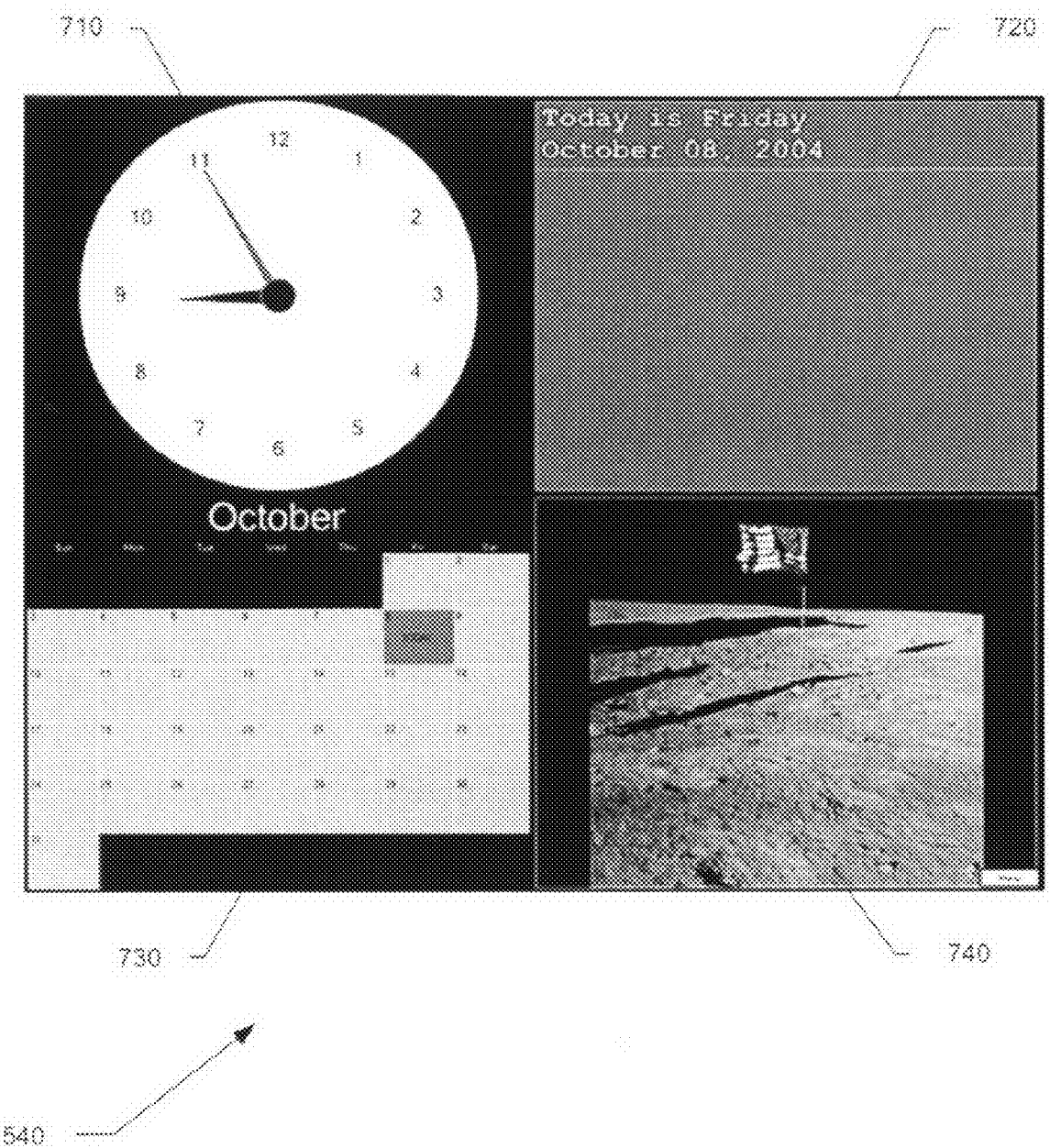
FIG. 6 is a depiction of a graphical user interface of the care receiver client.

Turning now to FIG. 6, care receiver client 422 will be discussed in further detail including the operations of care receiver client 422 in the methods of the current invention. One example of a customized graphical user interface 540 displayed on monitor 112 is shown in FIG. 6. As shown, one embodiment of the current invention utilizes graphical user interface 540 having preferably four zones or quadrants: a clock quadrant 710, a current month calendar quadrant 720, a reminders quadrant 730 which also displays the current date and day of the week, and a slideshow quadrant 740. Graphical user interface 540 also provides for videoconferencing by overlaying the video on a quadrant selected by the caregiver. When a videoconference concludes, the care receiver client 422 automatically refreshes graphical user interface 540.

As noted above, care receiver client 422 may operate in either attended or unattended mode. The operational mode is selected by one of the caregivers having the necessary privileges to change the operational characteristics of care receiver client 422. When operating in the unattended mode, care receiver's personal computer 115 is dedicated to running care receiver system 120 and care receiver monitor 112 continually displays the care receiver's graphical user interface 540 as shown in FIG. 6. In the unattended mode, the care receiver is not expected to provide any input or have any computer knowledge or skills. Even "to do" reminders do not require acknowledgment from the care receiver in unattended mode. As shown in FIG. 6, the quadrant labeled item 730 displays reminders, providing information to the care receiver and notifying the care receiver of tasks to be performed during the course of the day. The reminder box also displays the day, month and year. Reminders will appear below the date identifier in the manner formatted by the caregiver. As previously noted, the caregiver determines the format for displaying "to do" and "special" reminders. For example, in the box beneath the date indicator, either the background or the reminder text may flash. Additionally, a distinctive chime or pre-recorded message in the caregiver's voice may be played during display of the reminder.

Quadrant 710 displays a clock in either an analog or digital format. The presence of the clock helps the care receiver keep track of the time of day, but also helps make the graphical user interface an integral source of information for the care receiver.

Quadrant 730 displays the current month calendar. This helps the care receiver keep track of the current month and day of the month. As shown in quadrant 730 the current date is shaded differently from the remainder of the calendar month to highlight today's date.

Quadrant 740 provides the area for showing slideshows and displaying images. As discussed above, the slideshows are created by the caregiver. Subsequently slideshows are downloaded to care receiver database 425 for display on care receiver's system 120. In the preferred embodiment of the current invention slideshows run continuously, including being simultaneously displayed during a videoconference. During videoconferencing, a quadrant other than quadrant 740 is preferably selected for displaying the interactive videoconference. In the preferred embodiment, the quadrant used for the videoconference is pre-selected by the caregiver prior to establishing a videoconference in order to permit the care receiver and caregiver to discuss data displayed in the other three quadrants deemed most important to have visible during the videoconference.

If care receiver client 422 operates in attended mode, then the care receiver is expected to respond to messages generated by remote caregiver support system 100. Further, when operated in the attended mode, the care receiver's computer is assumed to be used for purposes in addition to running the remote caregiver support system 100. Thus, the care receiver has the ability to operate the computer in a normal manner running e-mail, browsing the internet or operating word processing systems in a normal manner. Additionally, when in attended mode, the care receiver has the option of establishing privacy periods during which care receivers prefer not to videoconference or otherwise be disturbed. Caregivers are informed of the preference when they attempt to establish a videoconference and may choose to disregard or override the preference.

When in the attended mode, care receiver client 422 operates in a manner similar to that of the unattended mode. However, in the attended mode, reminders require an additional degree of interaction between the care receiver and care receiver client 422. Specifically, in the attended mode the care receiver is expected to respond to messages which appear in a pop-up window which requires an affirmative action by the care receiver in order to clear the pop-up window. For example, a typical reminder may be scheduling of medication on a daily basis. If the medication is to be taken at a specific time of day, the pop-up window will appear with reminder text along with the designated chime or audio recording alerting the care receiver of the need to take the medication. The care receiver preferably takes the medication as indicated by the reminder and subsequently acknowledges to the care receiver client 422 the completion of the task in the reminder pop-up window. With the acknowledgement, the pop-up window is closed. While the preferred embodiment uses a pop-up window for reminders, an alternative embodiment may extend and use a portion of the main window of the care receiver's graphic user interface 540 to display the reminders.

As an additional feature, when operating in the attended mode, responses to and non-responses to reminder messages are logged in a journal maintained by care receiver client 422. This journal, as discussed above, is accessible by caregivers having the appropriate permissions. Thus, the current invention provides the means to not only remind the care receiver of the need for taking medications but also enables the caregiver to remotely monitor medication compliance. In the preferred embodiment, the journal stores all unacknowledged "to do" reminders and displays recent unacknowledged reminders. The caregiver may review the unacknowledged reminders and take appropriate action.

Finally, as noted above, care receiver system 120 includes EEMS 124 and the ANS client 424. FIG. 7 depicts a computer flow diagram of one preferred embodiment of the current invention showing the interaction of the EEMS client 423 and the ANS client 424. When these systems are active, data is collected by various sensors 127 over a hard-wired or wireless system. The data is transmitted to the EEMS server 126 and subsequently forwarded to care receiver system 120. Preferably, EEMS server 126 collects the sensor data and sends it to care receiver system 120. Subsequently, EEMS client 423, running on care receiver system 120, collects the data and records it in CR database 425. Optionally, data may be temporarily stored on the EEMS server 126 until the occurrence of a specific event or passage of a predetermined time interval. Upon the occurrence of the event or passage of time, the data is transmitted to the care receiver system and stored in the care receiver database 425. ANS client 424 analyzes the sensor data and informs the caregiver client 427 of the caregiver system 110 of environmental conditions in the care receiver's residence and alarm or alert conditions detected. For example, if smoke is detected by sensor 127, then an alert is preferably transmitted by ANS client 424 to caregiver system 110 and/or other designated communication device such as to the caregiver's mobile phone, e-mail address and other pre-designated contacts. Similarly, alerts may be generated for other events such as a door ajar after a specified time of day. The alert directed to the caregiver is preferably generated by care receiver system 120. FIG. 7 depicts a flow chart of the operation of EEMS 124 and ANS client 424 according to one preferred embodiment of the current invention.

In a preferred embodiment, the ANS client 424 generates alerts that are classified as "watch" or "warning" notices alerting the caregiver to a condition which may require action or follow-up. For example, a "watch" notice might be triggered when sensor 127 detects a temperature in the care receiver's residence outside of the programmed "normal" range. A "warning" notice might be triggered when the analysis of the temperature sensor 127 data detects that the temperature has been outside the "normal" range for a predetermined period of time or approaching a dangerous level. Caregivers defined to receive the alerts are notified in priority sequence as determined by the primary caregiver. As noted above, notice is provided in the form selected by the caregiver. For example, caregivers may receive emails, including email sent to mobile phones, or telephone messages.

The current invention has been described with specific reference to certain preferred embodiments; however, other embodiments of the current invention will be apparent to those skilled in the art from a consideration of this specification or practice of the invention disclosed herein. As such, the foregoing specification is considered merely exemplary of the current invention with the true scope and spirit of the invention being indicated by the following claims.

What is claimed:

1. A non-medical system comprising:
   a caregiver system;
   a care receiver system to facilitate remote informal care for at least one care receiver; and,
   a communication network linking the caregiver system and the care receiver system;
   wherein the care receiver system is operable in an unattended mode to enable operation of the care receiver system without any input on the part of the care receiver whereby the care receiver provides no input to and interacts with the care receiver system.

2. The system of claim 1 wherein the care receiver system is operable in an attended mode whereby the care receiver provides an input to and interacts with the care receiver system.

3. The system of claim 2 wherein the input enables the care receiver to acknowledge a reminder.

4. The system of claim 2 wherein the input enables the care receiver to accept, reject and initiate a videoconference.

5. The system of claim 1 further comprising:
   a care receiver client enabling interaction between the caregiver system and the care receiver system; and a caregiver client for accessing and configuring the care receiver system.

6. The system of claim 5 wherein the caregiver client accesses and configures a graphical user interface of the care receiver system.

7. The system of claim 5 wherein the caregiver client enables a caregiver to establish a videoconference with the care receiver system, the videoconference establishable in an interactive mode or an observational mode.

8. The system of claim 5 wherein the caregiver client enables the creation, editing and display of a slideshow on the care receiver system.

9. The system of claim 5 wherein the caregiver client enables the creation, editing and display of a reminder on the care receiver system.

10. The system of claim 9 wherein the display of the reminder is accompanied by an audible tone to draw attention to the reminder.

11. The system of claim 9 wherein the reminder is accompanied by a recording of the caregiver's voice.

12. The system of claim 9 wherein the reminder is accompanied by a visual cue.

13. The system of claim 9 wherein the care receiver system further comprises a database storing the reminder and any acknowledgement to the reminder generated by the care receiver system.

14. The system of claim 5 further comprising a plurality of global settings on the care receiver system adjustable by the caregiver client.

15. The system of claim 5 further comprising a plurality of multimedia settings dynamically adjustable by the caregiver client.

16. The system of claim 5 further comprising a client server monitor for monitoring operation of the care receiver client and automatically restarting the care receiver client if the care receiver client is detected to be unresponsive or operating outside of predetermined parameters.

17. The system of claim 1 further comprising a sensor for initiating a signal to be transmitted to an environment and event monitoring system, the signal analyzed against predetermined criteria to determine whether an alert should be issued.

18. The system of claim 17 further comprising an alert notification system client for transmitting the alert to a communication device designated by the caregiver.

19. The system of claim 1 wherein a graphical user interface of the care receiver system has at least two areas for displaying at least two of the following informational displays: a calendar, a clock, a reminder and a slideshow.

20. The system of claim 1 wherein the caregiver system can be assigned permissions to establish a plurality of functions the caregiver can perform.

21. A method of providing remote informal care to a care receiver comprising:
   establishing communication via a network between: a caregiver system having a caregiver client; and a care receiver system having a care receiver client;
   remotely configuring the care receiver client to facilitate remote informal care of the care receiver; and,
   providing at least one of the groups of: establishing a reminder setting on the care receiver system; establishing a videoconference between the care receiver system and the caregiver system; displaying a slideshow on the care receiver system; and establishing a journal entry on the care receiver system.

22. The method of claim 21 further comprising operating the care receiver system in an unattended mode to enable operation of the care receiver system without any input on the part of the care receiver whereby the care receiver provides no input to and interacts with the care receiver system.

23. The method of claim 21 further comprising the care receiver acknowledging the reminder by providing the input or initiating the videoconference by the care receiver by providing the input.

24. The method of claim 21 further comprising automatically restarting the care receiver client when the care receiver client is detected to be unresponsive or operating outside of predetermined parameters.

25. The method of claim 21 further comprising accessing and remotely configuring a graphical user interface of the care receiver system.

26. The method of claim 21 further comprising establishing the videoconference in multiple types of modes including an interactive mode and an observational mode.

27. The method of claim 26 further comprising switching from the observational mode to the interactive mode.

28. The method of claim 21 further comprising using the caregiver client to create, edit and display the slideshow on the care receiver system.

29. The method of claim 21 further comprising using the caregiver client to create, edit and display the reminder on the care receiver system.

30. The method of claim 29 wherein the display of the reminder is accompanied by an audible tone to draw attention to the reminder.

31. The method of claim 29 wherein the reminder is accompanied by a recording of a caregiver's voice.

32. The method of claim 29 wherein the reminder is accompanied by a visual cue.

33. The method of claim 21 further comprising storing in a database the reminder and any acknowledgement to the reminder generated by the care receiver system.

34. The method of claim 21 further comprising remotely adjusting a plurality of global settings on the care receiver system.

35. The method of claim 21 further comprising remotely and dynamically adjusting a plurality of multimedia settings on the care receiver system.

36. The method of claim 21 further comprising initiating a signal to be transmitted to an environment and event monitoring system, the signal analyzed against predetermined criteria to determine whether an alert should be issued.

37. The method of claim 36 further comprising an alert notification system client transmitting the alert to a communication device designated by a caregiver.

38. The method of claim 21 further comprising assigning permissions to the caregiver system to establish a plurality of care receiver functions a caregiver can perform.

39. A method of providing informal care to at least one care receiver at a separate location from a caregiver comprising:
communicating via a network between a caregiver system and a care receiver system to provide informal care to the at least one care receiver, the care receiver system comprising a care receiver client; and
establishing multiple types of videoconferences between the caregiver system and the care receiver system wherein the types of videoconferences include an interactive mode and an observational mode.

40. The method of claim 39 further comprising resetting the videoconference on the care receiver system with a caregiver client associated with the caregiver system.

41. The method of claim 39 further comprising switching from the observational mode to the interactive mode.

42. The method of claim 39 wherein the network is a virtual private network.

43. The method of claim 42 further comprising resetting the virtual private network using the caregiver client.

44. The method of claim 39 further comprising automatically restarting the care receiver client when the care receiver client is detected to be unresponsive or operating outside of predetermined parameters.

45. The method of claim 39 further comprising operating the care receiver system in an unattended mode to enable operation of the care receiver system without any input on the part of the care receiver whereby the care receiver provides no input to and interacts with the care receiver system.

46. The method of claim 39 further comprising operating the care receiver system in an attended mode whereby the care receiver provides an input to and interacts with the care receiver system.

47. The method of claim 39 further comprising: establishing a reminder on the care receiver system; displaying a slideshow on the care receiver system; and establishing a journal entry on the care receiver system.

48. The method of claim 47 wherein the reminder is accompanied by a recording of the caregiver's voice.

49. The method of claim 47 wherein the reminder is accompanied by a visual cue.

50. The method of claim 47 further comprising storing in a database the reminder and any acknowledgement to the reminder generated by the care receiver system.

51. The method of claim 39 further comprising remotely adjusting a plurality of global settings on the care receiver system.

52. The method of claim 39 further comprising dynamically and remotely adjusting a plurality of multimedia settings on the care receiver system.

53. The method of claim 39 further comprising initiating a signal to be transmitted to an environment and event monitoring system, the signal analyzed against predetermined criteria to determine whether an alert should be issued.

54. The method of claim 53 further comprising an alert notification system client transmitting the alert to a communication device designated by the caregiver.

55. The method of claim 39 further comprising assigning permissions to the caregiver system to establish a plurality of functions the caregiver can perform.

* * * * *